United States Patent
Estera et al.

(10) Patent No.: US 11,051,866 B2
(45) Date of Patent: Jul. 6, 2021

(54) COMBINATION ULTRASONIC AND ELECTROSURGICAL INSTRUMENT HAVING ULTRASONIC WAVEGUIDE WITH DISTAL OVERMOLD MEMBER

(71) Applicant: ETHICON LLC, Guaynabo, PR (US)

(72) Inventors: Frederick L. Estera, Cincinnati, OH (US); Michael A. Keenan, Cincinnati, OH (US); Craig T. Davis, Cincinnati, OH (US); William B. Weisenburgh, II, Maineville, OH (US); Jason R. Lesko, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 537 days.

(21) Appl. No.: 15/967,759

(22) Filed: May 1, 2018

(65) Prior Publication Data

US 2018/0333183 A1 Nov. 22, 2018

Related U.S. Application Data

(60) Provisional application No. 62/509,351, filed on May 22, 2017.

(51) Int. Cl.
*A61B 17/32* (2006.01)
*A61B 18/00* (2006.01)
(Continued)

(52) U.S. Cl.
CPC ...... *A61B 18/00* (2013.01); *A61B 17/320092* (2013.01); *A61B 18/1206* (2013.01);
(Continued)

(58) Field of Classification Search
CPC .... A61B 17/320068; A61B 17/320092; A61B 2017/00017; A61B 2017/00137;
(Continued)

(56) References Cited

U.S. PATENT DOCUMENTS 5,322,055 A 6/1994 Davison et al.
5,400,267 A 3/1995 Denen et al.
(Continued)

FOREIGN PATENT DOCUMENTS

DE 10 2014 116065 A1 5/2016
EP 2 371 314 A2 10/2011
(Continued)

OTHER PUBLICATIONS

U.S. Appl. No. 15/967,740, entitled "Combination Ultrasonic and Electrosurgical Instrument Having Electrical Circuits with Shared Return Path," filed May 1, 2018.
(Continued)

*Primary Examiner* — Jaymi E Della
*Assistant Examiner* — Khadijeh A Vahdat
(74) *Attorney, Agent, or Firm* — Frost Brown Todd LLC

(57) ABSTRACT

A surgical instrument includes an ultrasonic transducer, a shaft extending distally along a shaft axis, a waveguide acoustically coupled with the ultrasonic transducer and extending distally through the shaft, and an end effector at a distal end of the shaft. The end effector includes an ultrasonic blade acoustically coupled with the waveguide. A nodal support element is arranged within a distal portion of the shaft and encircles the waveguide at a distal-most acoustic node of the waveguide. The nodal support element includes a support portion aligned with the distal-most acoustic node, and a sealing portion extending axially from the support portion. The support portion engages an inner surface of the shaft and is configured to support the waveguide in coaxial alignment with the shaft axis. The sealing portion sealingly engages the inner surface of the shaft and is configured to prevent proximal ingress of fluid through the shaft.

20 Claims, 8 Drawing Sheets

(51) Int. Cl.
*A61B 18/12* (2006.01)
*A61B 18/14* (2006.01)
A61B 17/00 (2006.01)
A61B 17/29 (2006.01)
A61B 90/00 (2016.01)

(52) U.S. Cl.
CPC .............. *A61B 18/1445* (2013.01);
A61B 2017/00017 (2013.01); A61B
2017/00137 (2013.01); A61B 2017/2929
(2013.01); A61B 2017/2932 (2013.01); A61B
2017/320072 (2013.01); A61B 2017/320074
(2017.08); A61B 2017/320075 (2017.08);
A61B 2017/320078 (2017.08); A61B
2017/320088 (2013.01); A61B 2017/320094
(2017.08); A61B 2017/320095 (2017.08);
A61B 2018/0063 (2013.01); A61B 2018/00077
(2013.01); A61B 2018/00083 (2013.01); A61B
2018/00607 (2013.01); A61B 2018/00988
(2013.01); A61B 2018/00994 (2013.01); A61B
2018/126 (2013.01); A61B 2018/1452
(2013.01); A61B 2018/1457 (2013.01); A61B
2090/0803 (2016.02)

(58) Field of Classification Search
CPC ........... A61B 2017/00738; A61B 2017/00929;
A61B 2017/2929; A61B 2017/2932;
A61B 2017/320072; A61B 2017/320074;
A61B 2017/320075; A61B 2017/320078;
A61B 2017/320088; A61B 2017/320094;
A61B 2017/320095; A61B 18/00; A61B
18/1206; A61B 18/14; A61B 18/1445;
A61B 2018/00077; A61B 2018/00083;
A61B 2018/00136; A61B 2018/00178;
A61B 2018/00577; A61B 2018/00607;
A61B 2018/0063; A61B 2018/00988;
A61B 2018/00994; A61B 2018/126;
A61B 2018/142; A61B 2018/1452; A61B
2018/1457; A61B 2090/0803
See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 5,873,873 A | 2/1999 | Smith et al. | |
| 5,878,193 A | 3/1999 | Wang et al. | |
| 5,944,737 A * | 8/1999 | Tsonton | A61B 17/320092 606/205 |
| 5,980,510 A | 11/1999 | Tsonton et al. | |
| 6,231,565 B1 | 5/2001 | Tovey et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,364,888 B1 | 4/2002 | Niemeyer et al. | |
| 6,423,082 B1 | 7/2002 | Houser et al. | |
| 6,500,176 B1 | 12/2002 | Truckai et al. | |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,524,320 B2 | 4/2009 | Tierney et al. | |
| 7,691,098 B2 | 4/2010 | Wallace et al. | |
| 7,806,891 B2 | 10/2010 | Nowlin et al. | |
| 8,025,630 B2 | 9/2011 | Murakami et al. | |
| 8,057,498 B2 | 11/2011 | Robertson | |
| 8,147,488 B2 | 4/2012 | Masuda | |
| 8,461,744 B2 | 6/2013 | Wiener et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,591,536 B2 | 11/2013 | Robertson | |
| 8,602,288 B2 | 12/2013 | Shelton, IV et al. | |
| 8,616,431 B2 | 12/2013 | Timm et al. | |
| 8,623,027 B2 | 1/2014 | Price et al. | |
| 8,663,220 B2 | 3/2014 | Wiener et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,939,974 B2 | 1/2015 | Boudreaux et al. | |
| 8,986,302 B2 | 3/2015 | Aldridge et al. | |
| 9,017,326 B2 | 4/2015 | DiNardo et al. | |
| 9,039,690 B2 | 5/2015 | Kersten et al. | |
| 9,089,327 B2 | 7/2015 | Worrell et al. | |
| 9,095,367 B2 | 8/2015 | Olson et al. | |
| 9,101,385 B2 | 8/2015 | Shelton, IV et al. | |
| 9,107,690 B2 | 8/2015 | Bales, Jr. et al. | |
| 9,161,803 B2 | 10/2015 | Yates et al. | |
| 9,301,759 B2 | 4/2016 | Spivey et al. | |
| 9,402,682 B2 | 8/2016 | Worrell et al. | |
| 9,545,253 B2 | 1/2017 | Worrell et al. | |
| 9,572,622 B2 | 2/2017 | Shelton, IV et al. | |
| 9,681,912 B2 | 6/2017 | Tsubuku et al. | |
| 9,901,754 B2 | 2/2018 | Yamada | |
| 9,962,222 B2 | 5/2018 | Brustad et al. | |
| 10,010,340 B2 | 7/2018 | Hibner et al. | |
| 10,028,765 B2 | 7/2018 | Hibner et al. | |
| 10,039,595 B2 | 8/2018 | Sakaguchi et al. | |
| 10,201,364 B2 | 2/2019 | Leimbach et al. | |
| 2012/0078243 A1 | 3/2012 | Worrell et al. | |
| 2014/0135804 A1 | 5/2014 | Weisenburgh, II et al. | |
| 2014/0163541 A1 | 6/2014 | Shelton, IV et al. | |
| 2014/0239037 A1 | 8/2014 | Boudreaux et al. | |
| 2015/0088178 A1 | 3/2015 | Stulen et al. | |
| 2015/0141981 A1 | 5/2015 | Price et al. | |
| 2015/0245850 A1* | 9/2015 | Hibner | A61B 18/1482 606/171 |
| 2015/0358426 A1 | 12/2015 | Kimball et al. | |
| 2015/0374360 A1 | 12/2015 | Scheib et al. | |
| 2016/0022305 A1 | 1/2016 | Lamping et al. | |
| 2016/0302820 A1 | 10/2016 | Hibner et al. | |
| 2016/0324537 A1 | 11/2016 | Green et al. | |
| 2016/0367281 A1 | 12/2016 | Gee et al. | |
| 2017/0000515 A1 | 1/2017 | Akagane | |
| 2017/0000516 A1 | 1/2017 | Stulen et al. | |
| 2017/0000541 A1 | 1/2017 | Yates et al. | |
| 2017/0086876 A1 | 3/2017 | Wiener et al. | |
| 2017/0086908 A1 | 3/2017 | Wiener et al. | |
| 2017/0086909 A1 | 3/2017 | Yates et al. | |
| 2017/0086910 A1 | 3/2017 | Wiener et al. | |
| 2017/0086911 A1 | 3/2017 | Wiener et al. | |
| 2017/0105754 A1 | 4/2017 | Boudreaux et al. | |
| 2018/0116688 A1 | 5/2018 | Akagane | |
| 2018/0333182 A1 | 11/2018 | Clauda | |

FOREIGN PATENT DOCUMENTS

| | | |
|---|---|---|
| EP | 2 478 861 A2 | 7/2012 |
| EP | 2 641 552 A2 | 9/2013 |
| EP | 3 031 417 A1 | 6/2016 |
| EP | 3 117 790 A1 | 1/2017 |
| EP | 3 287 085 A1 | 2/2018 |
| WO | WO 2016/091400 A1 | 6/2016 |
| WO | WO 2017/027853 A1 | 2/2017 |
| WO | WO 2017/058617 A2 | 4/2017 |

(56) References Cited

FOREIGN PATENT DOCUMENTS

WO   WO 2017/091377 A1   6/2017
WO   WO 2017/100427 A2   6/2017

OTHER PUBLICATIONS

U.S. Appl. No. 15/967,746, entitled "Combination Ultrasonic and Electrosurgical Instrument Having Slip Ring Electrical Contact Assembly," filed May 1, 2018.
U.S. Appl. No. 15/967,747, entitled "Combination Ultrasonic and Electrosurgical Instrument Having Electrically Insulating Features," filed May 1, 2018.
U.S. Appl. No. 15/967,751, entitled "Combination Ultrasonic and Electrosurgical Instrument Having Curved Ultrasonic Blade," filed May 1, 2018.
U.S. Appl. No. 15/967,753, entitled "Combination Ultrasonic and Electrosurgical Instrument Having Clamp Arm Electrode," filed May 1, 2018.
U.S. Appl. No. 15/967,761, entitled "Combination Ultrasonic and Electrosurgical System Having Generator Filter Circuitry," filed May 1, 2018.
U.S. Appl. No. 15/967,763, entitled "Combination Ultrasonic and Electrosurgical Instrument with Adjustable Energy Modalities and Method for Sealing Tissue and Inhibiting Tissue Resection," filed May 1, 2018.
U.S. Appl. No. 15/967,764, entitled "Combination Ultrasonic and Electrosurgical System Having EEPROM and ASIC Components," filed May 1, 2018.
U.S. Appl. No. 15/967,770, entitled "Combination Ultrasonic and Electrosurgical Instrument with a Production Clamp Force Based Ultrasonic Seal Process and Related Methods," filed May 1, 2018.
U.S. Appl. No. 15/967,775, entitled "Combination Ultrasonic and Electrosurgical Instrument with Adjustable Energy Modalities and Method for Limiting Blade Temperature," filed May 1, 2018.
U.S. Appl. No. 15/967,777, entitled "Combination Ultrasonic and Electrosurgical Instrument and Method for Sealing Tissue with Various Termination Parameters," filed May 1, 2018.
U.S. Appl. No. 15/967,784, entitled "Combination Ultrasonic and Electrosurgical Instrument and Method for Sealing Tissue in Successive Phases," filed May 1, 2018.
U.S. Appl. No. 15/967,740.
U.S. Appl. No. 15/967,746.
U.S. Appl. No. 15/967,747.
U.S. Appl. No. 15/967,751.
U.S. Appl. No. 15/967,753.
U.S. Appl. No. 15/967,761; and.
U.S. Appl. No. 15/967,764.
International Search Report and Written Opinion dated Aug. 22, 2018 for Application No. PCT/US2018/033599, 14 pgs.
International Search Report and Written Opinion dated Jan. 2, 2019 for Application No. PCT/US2018/033603, 23 pgs.
International Search Report and Written Opinion dated Nov. 6, 2018 for Application No. PCT/US2018/033605, 14 pgs.
International Search Report and Written Opinion dated Jan. 2, 2019 for Application No. PCT/US2018/033607, 22 pgs.
International Search Report and Written Opinion dated Nov. 6, 2018 for Application No. PCT/US2018/033608, 14 pgs.
International Search Report and Written Opinion dated Sep. 3, 2018 for Application No. PCT/US2018/033615, 13 pgs.
International Search Report and Written Opinion dated Aug. 22, 2018 for Application No. PCT/US2018/033618, 12 pgs.
International Search Report and Written Opinion dated Oct. 19, 2018 for Application No. PCT/US2018/033619, 20 pgs.
U.S. Appl. No. 62/509,351, entitled "Ultrasonic Instrument With Electrosurgical Features," filed May 22, 2017.

\* cited by examiner

//COMBINATION ULTRASONIC AND ELECTROSURGICAL INSTRUMENT HAVING ULTRASONIC WAVEGUIDE WITH DISTAL OVERMOLD MEMBER

This application claims the benefit of U.S. Provisional App. No. 62/509,351, entitled "Ultrasonic Instrument With Electrosurgical Features," filed May 22, 2017, the disclosure of which is incorporated by reference herein.

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit lower frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

While various types of ultrasonic surgical instruments and electrosurgical instruments, including combination ultrasonic-electrosurgical instruments, have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
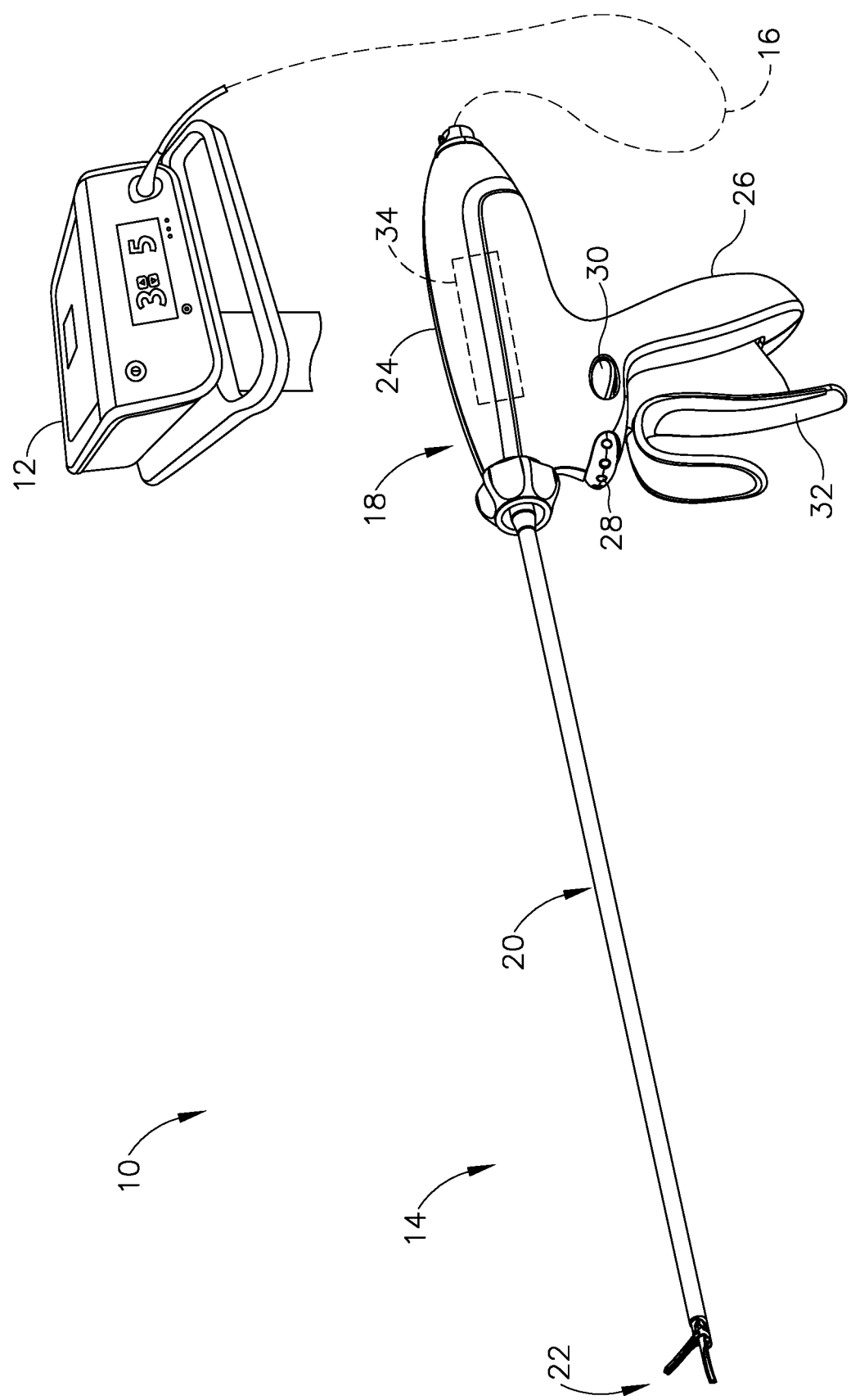
FIG. 1 depicts a perspective view of an exemplary surgical system having a generator and a surgical instrument operable to treat tissue with ultrasonic energy and bipolar RF energy.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Surgical System

FIG. 1 depicts an exemplary surgical system (10) including a generator (12) and a surgical instrument (14). Surgical instrument (14) is operatively coupled with the generator (12) via power cable (16). As described in greater detail below, generator (12) is operable to power surgical instrument (14) to deliver ultrasonic energy for cutting tissue, and electrosurgical bipolar RF energy (i.e., therapeutic levels of RF energy) for sealing tissue. In exemplary configurations, generator (12) is configured to power surgical instrument (14) to deliver ultrasonic energy and electrosurgical bipolar RF energy simultaneously.

A. Overview of Exemplary Surgical Instrument with Ultrasonic and Electrosurgical Features Surgical instrument (14) of the present example comprises a handle assembly (18), a shaft assembly (20) extending distally from the handle assembly (18), and an end effector (22) arranged at a distal end of the shaft assembly (20). Handle assembly (18) comprises a body (24) including a pistol grip (26) and energy control buttons (28, 30) configured to be manipulated by a surgeon. A trigger (32) is coupled to a lower portion of body (24) and is pivotable toward and away from pistol grip (26) to selectively actuate end effector (22), as described in greater detail below. In other suitable variations of surgical instrument (14), handle assembly (18) may comprise a scissor grip configuration, for example. As described in greater detail below, an ultrasonic transducer (34) is housed internally within and supported by body (24). In other configurations, ultrasonic transducer (34) may be provided externally of body (24).

Figure 2:
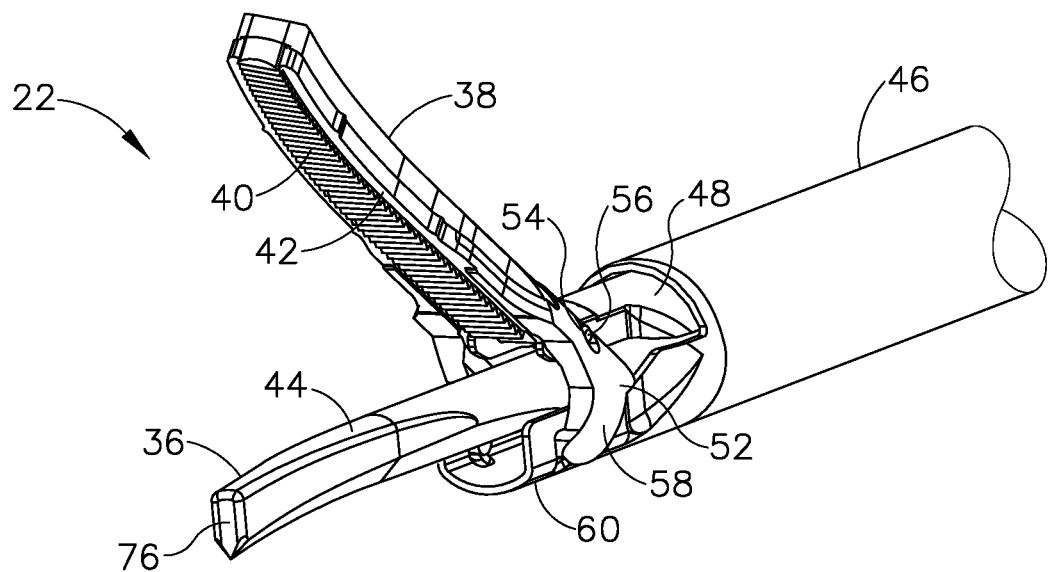
FIG. 2 depicts a top perspective view of an end effector of the surgical instrument of FIG. 1, having a clamp arm that provides a first electrode and an ultrasonic blade that provides a second electrode.
Figure 3:
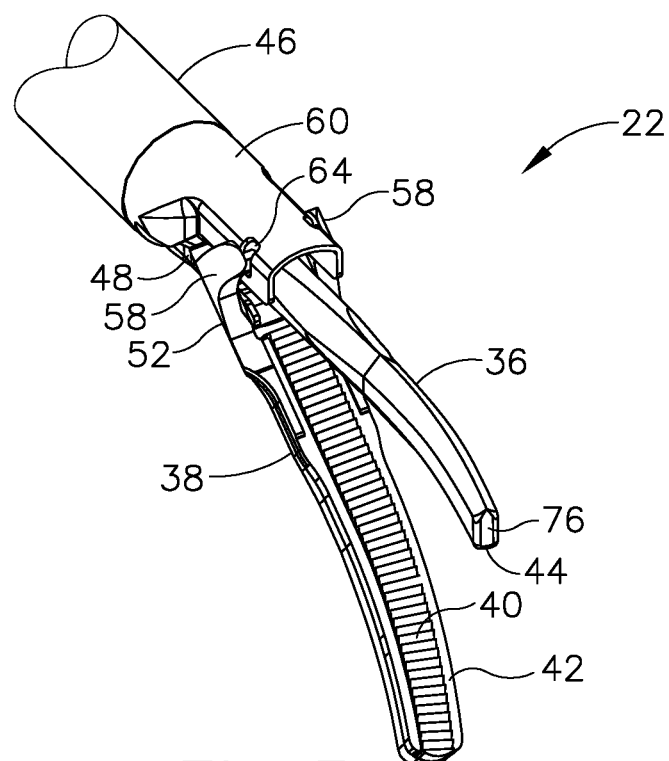
FIG. 3 depicts a bottom perspective view of the end effector of FIG. 2.

As shown in FIGS. 2 and 3, end effector (22) includes an ultrasonic blade (36) and a clamp arm (38) configured to selectively pivot toward and away from ultrasonic blade (36), for clamping tissue therebetween. Ultrasonic blade (36) is acoustically coupled with ultrasonic transducer (34), which is configured to drive (i.e., vibrate) ultrasonic blade (36) at ultrasonic frequencies for cutting and/or sealing tissue positioned in contact with ultrasonic blade (36). Clamp arm (38) is operatively coupled with trigger (32) such that clamp arm (38) is configured to pivot toward ultrasonic blade (36), to a closed position, in response to pivoting of trigger (32) toward pistol grip (26). Further, clamp arm (38) is configured to pivot away from ultrasonic blade (36), to an open position (see e.g., FIGS. 1-3), in response to pivoting of trigger (32) away from pistol grip (26). Various suitable ways in which clamp arm (38) may be coupled with trigger (32) will be apparent to those of ordinary skill in the art in view of the teachings provided herein. In some versions, one or more resilient members may be incorporated to bias clamp arm (38) and/or trigger (32) toward the open position.

A clamp pad (40) is secured to and extends distally along a clamping side of clamp arm (38), facing ultrasonic blade (36). Clamp pad (40) is configured to engage and clamp tissue against a corresponding tissue treatment portion of ultrasonic blade (36) when clamp arm (38) is actuated to its closed position. At least a clamping-side of clamp arm (38) provides a first electrode (42), referred to herein as clamp arm electrode (42). Additionally, at least a clamping-side of ultrasonic blade (36) provides a second electrode (44), referred to herein as blade electrode (44). As described in greater detail below, electrodes (42, 44) are configured to apply electrosurgical bipolar RF energy, provided by generator (12), to tissue electrically coupled with electrodes (42, 44). Clamp arm electrode (42) may serve as an active electrode while blade electrode (44) serves as a return electrode, or vice-versa. Surgical instrument (14) may be configured to apply the electrosurgical bipolar RF energy through electrodes (42, 44) while vibrating ultrasonic blade (36) at an ultrasonic frequency, before vibrating ultrasonic blade (36) at an ultrasonic frequency, and/or after vibrating ultrasonic blade (36) at an ultrasonic frequency.

As shown in FIGS. 1-5, shaft assembly (20) extends along a longitudinal axis and includes an outer tube (46), an inner tube (48) received within outer tube (46), and an ultrasonic waveguide (50) supported within inner tube (48). As seen best in FIGS. 2-5, clamp arm (38) is coupled to distal ends of inner and outer tubes (46, 48). In particular, clamp arm (38) includes a pair of proximally extending clevis arms (52) that receive therebetween and pivotably couple to a distal end (54) of inner tube (48) with a pivot pin (56) received within through bores formed in clevis arms (52) and distal end (54) of inner tube (48). First and second clevis fingers (58) depend downwardly from clevis arms (52) and pivotably couple to a distal end (60) of outer tube (46). Specifically, each clevis finger (58) includes a protrusion (62) that is rotatably received within a corresponding opening (64) formed in a sidewall of distal end (60) of outer tube (46).

In the present example, inner tube (48) is longitudinally fixed relative to handle assembly (18), and outer tube (46) is configured to translate relative to inner tube (48) and handle assembly (18), along the longitudinal axis of shaft assembly (20). As outer tube (46) translates distally, clamp arm (38) pivots about pivot pin (56) toward its open position. As outer tube (46) translates proximally, clamp arm (38) pivots in an opposite direction toward its closed position. A proximal end of outer tube (46) is operatively coupled with trigger (32), for example via a linkage assembly, such that actuation of trigger (32) causes translation of outer tube (46) relative to inner tube (48), thereby opening or closing clamp arm (38). In other suitable configurations not shown herein, outer tube (46) may be longitudinally fixed and inner tube (48) may be configured to translate for moving clamp arm (38) between its open and closed positions.

Shaft assembly (20) and end effector (22) are configured to rotate together about the longitudinal axis, relative to handle assembly (18). A retaining pin (66), shown in FIG. 4, extends transversely through proximal portions of outer tube (46), inner tube (48), and waveguide (50) to thereby couple these components rotationally relative to one another. In the present example, a rotation knob (68) is provided at a proximal end portion of shaft assembly (20) to facilitate rotation of shaft assembly (20), and end effector (22), relative to handle assembly (18). Rotation knob (68) is secured rotationally to shaft assembly (20) with retaining pin (66), which extends through a proximal collar of rotation knob (68). It will be appreciated that in other suitable configurations, rotation knob (68) may be omitted or substituted with alternative rotational actuation structures.

Figure 5:
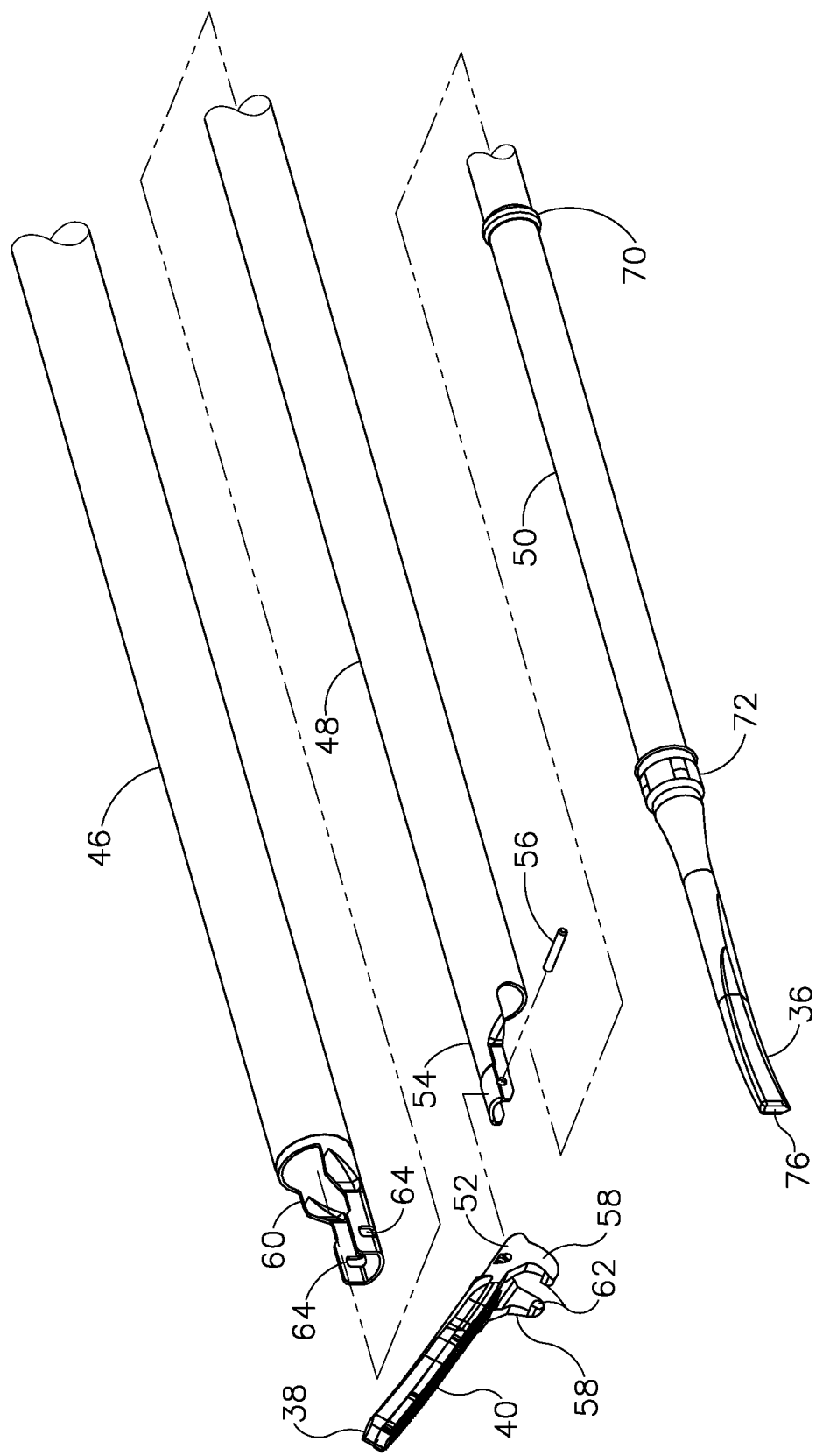
FIG. 5 depicts an enlarged exploded perspective view of a distal portion of the shaft assembly and the end effector of the surgical instrument of FIG. 1.

Ultrasonic waveguide (50) is acoustically coupled at its proximal end with ultrasonic transducer (34), for example by a threaded connection, and at its distal end with ultrasonic blade (36), as shown in FIG. 5. Ultrasonic blade (36) is shown formed integrally with waveguide (50) such that blade (36) extends distally, directly from the distal end of waveguide (50). In this manner, waveguide (50) acoustically couples ultrasonic transducer (34) with ultrasonic blade (36), and functions to communicate ultrasonic mechanical vibrations from transducer (34) to blade (36). Accordingly, ultrasonic transducer (34), waveguide (50), and ultrasonic blade (36) together define acoustic assembly (100). During use, ultrasonic blade (36) may be positioned in direct contact with tissue, with or without assistive clamping force provided by clamp arm (38), to impart ultrasonic vibrational energy to the tissue and thereby cut and/or seal the tissue. For example, blade (36) may cut through tissue clamped between clamp arm (38) and a first treatment side of blade (36), or blade (36) may cut through tissue positioned in contact with an oppositely disposed second treatment side of blade (36), for example during a "back-cutting" movement. In some variations, waveguide (50) may amplify the ultrasonic vibrations delivered to blade (36). Further, waveguide (50) may include various features operable to control the gain of the vibrations, and/or features suitable to tune waveguide (50) to a selected resonant frequency. Additional exemplary features of ultrasonic blade (36) and waveguide (50) are described in greater detail below.

Figure 4:
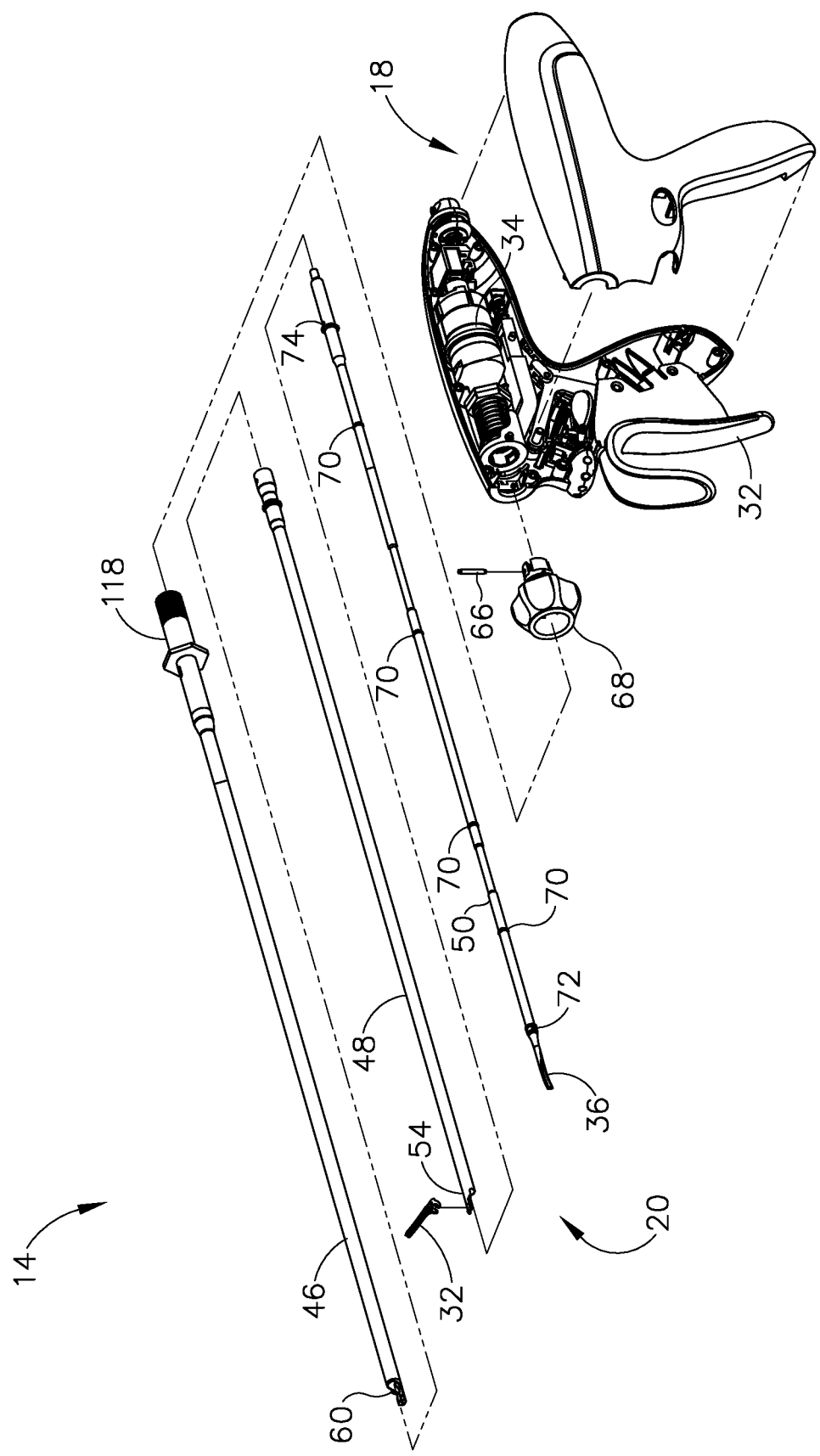
FIG. 4 depicts a partially exploded perspective view of the surgical instrument of FIG. 1.

Waveguide (50) is supported within inner tube (48) by a plurality of nodal support elements (70) positioned along a length of waveguide (50), as shown in FIGS. 4 and 5. Specifically, nodal support elements (70) are positioned longitudinally along waveguide (50) at locations corresponding to acoustic nodes defined by the resonant ultrasonic vibrations communicated through waveguide (50). Nodal support elements (70) may provide structural support to waveguide (50), and acoustic isolation between waveguide (50) and inner and outer tubes (46, 48) of shaft assembly (20). In exemplary variations, nodal support elements (70) may comprise o-rings. Waveguide (50) is supported at its distal-most acoustic node by a nodal support element in the form of an overmold member (72), shown in FIG. 5 and described in greater detail below with reference to FIG. 7. Waveguide (50) is secured longitudinally and rotationally within shaft assembly (20) by retaining pin (66), which passes through a transverse through-bore (74) formed at a proximally arranged acoustic node of waveguide (50), such as the proximal-most acoustic node, for example.

In the present example, a distal tip (76) of ultrasonic blade (36) is located at a position corresponding to an anti-node associated with the resonant ultrasonic vibrations communicated through waveguide (50). Such a configuration enables the acoustic assembly (100) of instrument (14) to be tuned to a preferred resonant frequency $f_o$ when ultrasonic blade (36) is not loaded by tissue. When ultrasonic transducer (34) is energized by generator (12) to transmit mechanical vibrations through waveguide (50) to blade (36), distal tip (76) of blade (36) is caused to oscillate longitudinally in the range of approximately 20 to 120 microns peak-to-peak, for example, and in some instances in the range of approximately 20 to 50 microns, at a predetermined vibratory frequency $f_o$ of approximately 50 kHz, for example. When ultrasonic blade (36) is positioned in contact with tissue, the ultrasonic oscillation of blade (36) may simultaneously sever the tissue and denature the proteins in adjacent tissue cells, thereby providing a coagulative effect with minimal thermal spread.

Figure 6:
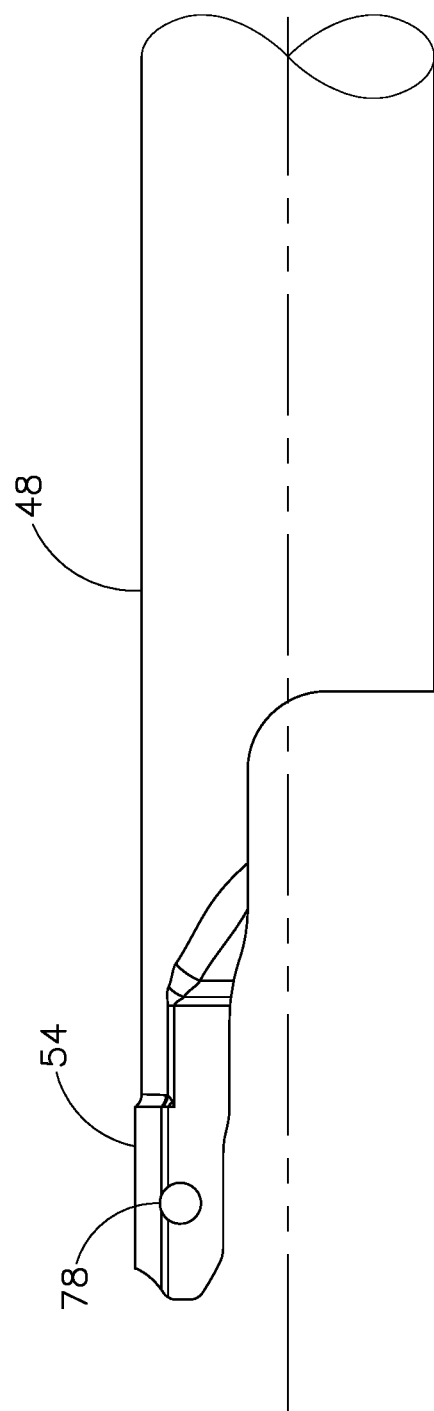
FIG. 6 depicts a side elevational view of a distal portion of an inner tube of the shaft assembly of the surgical instrument of FIG. 1.

As shown in FIG. 6, distal end (54) of inner tube (48) may be offset radially outwardly relative to a remaining proximal portion of inner tube (48). This configuration enables pivot pin bore (78), which receives clamp arm pivot pin (56), to be spaced further away from the longitudinal axis of shaft assembly (20) than if distal end (54) where formed flush with the remaining proximal portion of inner tube (48). Advantageously, this provides increased clearance between proximal portions of clamp arm electrode (42) and blade electrode (44), thereby mitigating risk of undesired "shorting" between electrodes (42, 44) and their corresponding active and return electrical paths, for example during back-cutting when ultrasonic blade (36) flexes toward clamp arm (38) and pivot pin (56) in response to normal force exerted on blade (36) by tissue. In other words, when ultrasonic blade (36) is used in a back-cutting operation, ultrasonic blade (36) may tend to deflect slightly away from the longitudinal axis of shaft assembly (20), toward pin (56). By having pivot pin bore (78) spaced further away from the longitudinal axis than pivot pin bore (78) otherwise would be in the absence of the radial offset provided by distal end (54) of the present example, distal end (54) provides additional lateral clearance between pivot pin (56) and ultrasonic blade (36), thereby reducing or eliminating the risk of contact between ultrasonic blade (36) and pivot pin (56) when ultrasonic blade (36) deflects laterally during back-cutting operations. In addition to preventing electrical short circuits that would otherwise result from contact between ultrasonic blade (36) and pivot pin (56) when end effector (22) is activated to apply RF electrosurgical energy, the additional clearance prevents mechanical damage that might otherwise result from contact between ultrasonic blade (36) and pivot pin (56) when ultrasonic blade (36) is vibrating ultrasonically.

B. Exemplary Overmold Member for Ultrasonic Waveguide

Figure 7:
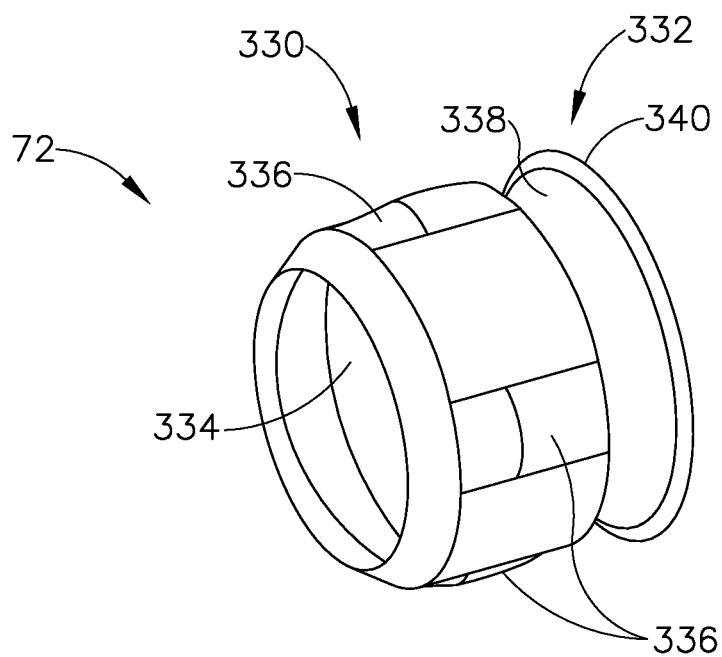
FIG. 7 depicts a perspective view of an exemplary nodal support element of the surgical instrument of FIG. 1, the nodal support element configured to support a waveguide of the surgical instrument at a distal-most acoustic node thereof.
Figure 8:
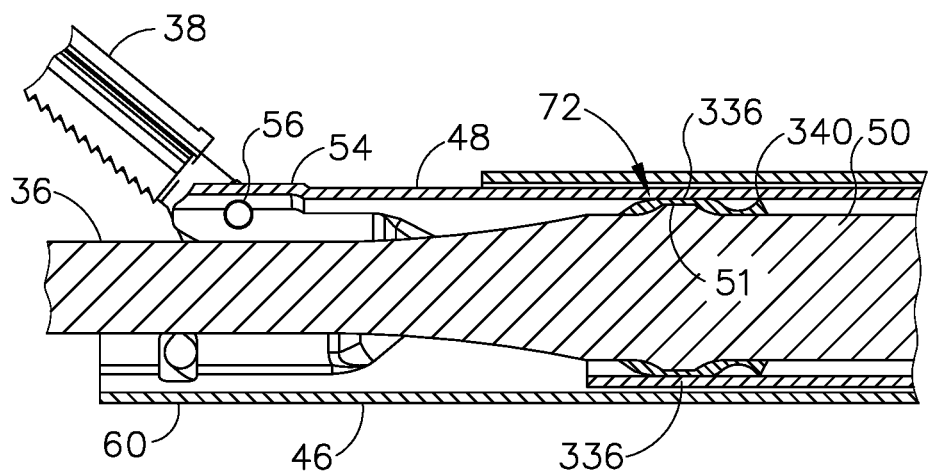
FIG. 8 depicts a side sectional view of the end effector and distal portion of the shaft assembly of the surgical instrument of FIG. 1, showing engagement of the nodal support element of FIG. 7 with the waveguide and inner tube of the shaft assembly.

FIGS. 7-9B show additional details of overmold member (72). As described above, overmold member (72) encircles waveguide (50) at a distal-most acoustic node thereof, thereby supporting waveguide (50) within inner tube (48) and defining a distal-most waveguide support location. As shown in FIG. 8, waveguide (50) includes an annular nodal flange (51) at its distal-most acoustic node, and overmold member (72) encircles nodal flange (51). Ultrasonic blade (36) is integrally joined to waveguide (50) at distal nodal flange (51) and extends distally therefrom.

As shown in FIG. 7, overmold member (72) includes a load bearing portion (330) and an integrally formed sealing portion (332) extending proximally from load bearing portion (330). As described below, each of load bearing support portion (330) and sealing portion (332) is configured to engage an inner surface of inner tube (48). Load bearing support portion (330) includes an inner annular groove (334) configured to receive distal nodal flange (51) of waveguide (50) in sealing engagement, such that load bearing support portion (330) aligns with and encircles distal nodal flange (51) while sealing portion (332) extends proximally of distal nodal flange (51).

Load bearing support portion (330) of overmold member (72) includes a plurality of deforming elements (336) spaced circumferentially about its exterior. Deforming elements (336) define a maximum outer diameter of load bearing portion (330) that is greater than an inner diameter of inner tube (48). Accordingly, deforming elements (336) are configured to resiliently deform against the inner surface of inner tube (48) so as to engage inner tube (48) with an interference fit. Circumferential spacing between deforming elements (336) enables elements (336) to deform in a circumferential direction along the inner surface of inner tube (48). In this manner, load bearing support portion (330) is configured to support waveguide (50) in coaxial alignment with the longitudinal axis of shaft assembly (20), and mitigate radial displacement of distal nodal flange (51) relative to the longitudinal axis when waveguide (50) is driven with ultrasonic energy, as described above. Advantageously, this prevents unwanted direct contact between ultrasonic blade (36) and clamp arm (38), or clamp arm pivot pin (56), which could otherwise cause mechanical failure of blade (36) and/or electrical shorting of an RF electrical circuit of surgical instrument (10). Overmold member (72) may be formed of any material or combination of materials suitable to acoustically isolate distal nodal flange (51) relative to inner tube (48). For instance, at least deforming elements (336) and sealing portion (332) may be formed of a resiliently deformable polymeric material, such as silicone, for example.

Each deforming element (336) is shown in the form of a rounded protrusion, or bump, integrally formed with load bearing support portion (330) and projecting radially outwardly from an outer surface thereof, and extending axially. As shown in FIGS. 7-9B, load bearing support portion (330) includes four deforming elements (336) arranged with uniform circumferential spacing. In other configurations, any suitable quantity and circumferential spacing of deforming elements (336) may be provided. As shown in FIG. 7, a distal end of load bearing support portion (330) may taper from deforming elements (336) toward ultrasonic blade (36).

Figure 9A:
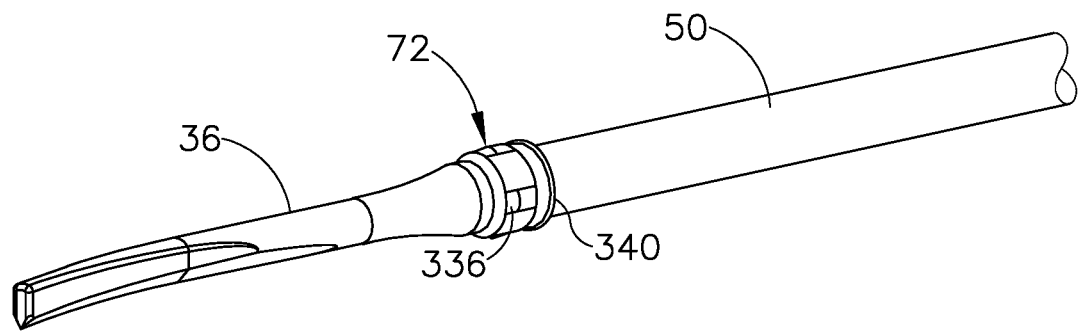
FIG. 9A depicts a perspective view of the nodal support element of FIG. 7 mounted on a distal portion of the waveguide of the surgical instrument of FIG. 1, proximally of the ultrasonic blade.
Figure 9B:
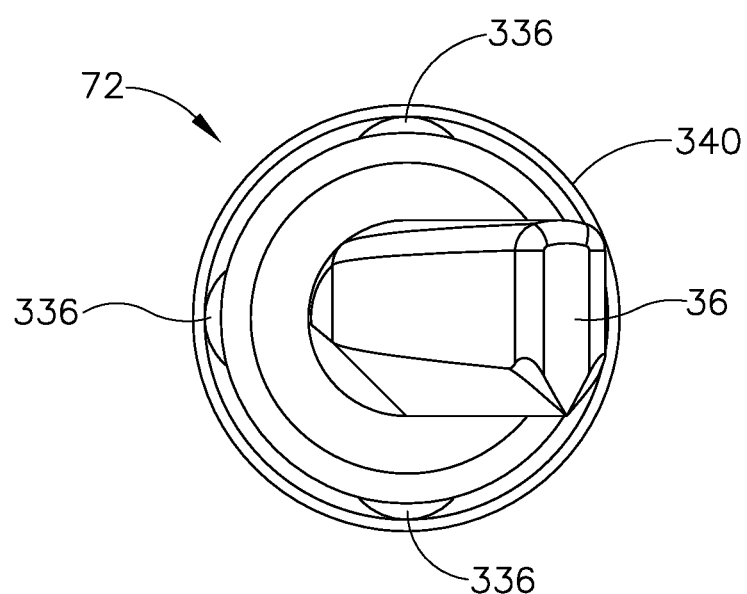
FIG. 9B depicts an end view of the nodal support element and the ultrasonic blade of FIG. 9A.

Sealing portion (332) of overmold member (72) is spaced proximally from load bearing support portion (330) by an outer annular groove (338). Sealing portion (332) includes an annular outer sealing edge (340) configured as a wiper seal that resiliently deforms against, and thereby establishes a liquid-tight seal with, a full inner circumference of the inner surface of inner tube (48). As shown, an axial dimension of sealing edge (340) is substantially less than an axial dimension of deforming elements (336). Accordingly, while deforming elements (336) are configured to provide structural support to waveguide (50), sealing edge (340) is configured to maintain a liquid-tight seal against inner tube (48) to prevent proximal ingress of body fluids and tissue into shaft assembly (20) along waveguide (50). Such ingress could yield undesirable reduction of ultrasonic energy delivery from waveguide (50) to ultrasonic blade (36), and/or electrical coupling of waveguide (50) to inner tube (48), which could result in shorting of the RF electrical circuit of surgical instrument (10). As shown in FIGS. 8 and 9B, outer sealing edge (340) defines a maximum outer diameter of sealing portion (332), which may be equal to, slightly less than, or slightly greater than the maximum outer diameter of load bearing portion (330) defined by deforming elements (336).

C. Exemplary Alternative Overmold Member for Ultrasonic Waveguide

Figure 10:
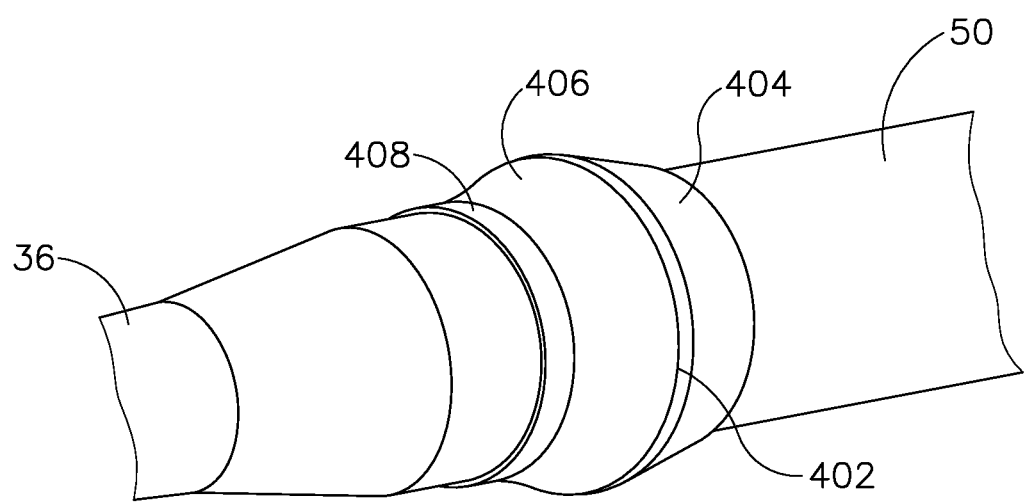
FIG. 10 depicts a perspective view of another exemplary nodal support element suitable for use with the surgical instrument of FIG. 1.

FIG. 10 shows another exemplary overmold member (400) suitable for use with surgical instrument (10) in place of overmold member (72). Overmold member (400) is similar to overmold member (72) described above except as otherwise described below. Similar to overmold member (72), overmold member (400) encircles nodal flange (51) at the distal-most acoustic node of waveguide (50) to thereby support waveguide (50) coaxially within inner tube (48). Unlike overmold member (72), an exterior of overmold member (400) includes an annular rim (402) that engages an inner surface of inner tube (48) with an interference fit so as to function as both a load bearing portion and a sealing portion, similar to load bearing portion (330) and sealing portion (332) of overmold member (72) described above.

Annular rim (402) of overmold member (400) of the present example is positioned at a medial portion of overmold member (400) such that annular rim (402) is aligned with distal nodal flange (51) of waveguide (50). Annular rim (402) extends continuously about a full circumference of overmold member (400) such that rim (402) is configured to establish a continuous seal with the inner surface of inner tube (48). Moreover, annular rim (402) extends radially outwardly to define a maximum outer diameter of overmold member (400) that provides a degree of interference with inner tube (48) sufficient to provide both mechanical support and annular sealing about the full circumference of waveguide (50). In some examples, annular rim (402) may provide a higher degree of interference with inner tube (48) than deforming elements (336) of overmold member (72). However, similar to deforming elements (50), at least annular rim (402) of overmold member (400) may be formed of a resiliently deformable polymeric material, such as silicone, for example. Though not shown, overmold member (400) may include one or more additional annular features arranged proximally or distally of annular rim (402) and configured to sealingly engage the inner surface of inner tube (48), for instance similar to annular sealing edge (340) described above.

Overmold member (400) of the present example further includes a proximal tapered portion (404) that extends proximally from annular rim (402), a distal tapered portion (406) that extends distally from annular rim (402), and a distal flap (408) that extends distally from a distal end of distal tapered portion (406). Proximal tapered portion (404) tapers inwardly from annular rim (402) in a proximal direction, and distal tapered portion (406) tapers inwardly from annular rim (402) in a distal direction. Proximal and distal tapered portions (404, 406) may be formed with similar axial lengths and taper angles and are configured to facilitate axial assembly of inner tube (48) over waveguide (50) and overmold member (400). Distal flap (408) overlaps a proximal end of ultrasonic blade (36) and is configured to create an annular seal between overmold member (400) and the corresponding portion of waveguide (50) and ultrasonic blade (36) covered by distal flap (408). It will be appreciated that various other versions of overmold member (72, 400) may be employed that incorporate one or more features from each of the overmold members (72, 400) to provide annular sealing and mechanical support about the circumference of waveguide (50) within inner tube (48).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an ultrasonic transducer; (b) a shaft extending distally relative to the ultrasonic transducer along a longitudinal shaft axis; (c) a waveguide acoustically coupled with the ultrasonic transducer and extending distally through the shaft; (d) an end effector arranged at a distal end of the shaft, wherein the end effector includes an ultrasonic blade acoustically coupled with the waveguide, wherein the ultrasonic transducer is operable to drive the waveguide and the ultrasonic blade with ultrasonic energy; and (e) a nodal support element arranged within a distal portion of the shaft, wherein the nodal support element encircles the waveguide at a distal-most acoustic node thereof, wherein the nodal support element comprises: (i) a support portion aligned with the distal-most acoustic node, wherein the support portion is configured to engage an inner surface of the shaft and thereby support the waveguide in coaxial alignment with the shaft axis, and (ii) a sealing portion extending axially from the support portion, wherein the sealing portion is configured to sealingly engage the inner surface of the shaft and thereby prevent proximal ingress of fluid through the shaft.

Example 2

The surgical instrument of Example 1, wherein the nodal support element comprises an overmold member.

Example 3

The surgical instrument of any of the previous Examples, wherein the support portion has a maximum outer diameter that is greater than an inner diameter of the shaft, wherein the support portion is configured to engage the inner surface of the shaft with an interference fit.

Example 4

The surgical instrument of any of the previous Examples, wherein the support portion includes a plurality of deformable elements spaced circumferentially about an exterior thereof, wherein the deformable elements are configured to deform against the inner surface of the shaft.

Example 5

The surgical instrument of Example 4, herein the deformable elements are resiliently deformable.

Example 6

The surgical instrument of any of Examples 4 through 5, wherein the deformable elements are arranged with uniform circumferential spacing.

Example 7

The surgical instrument of any of Examples 4 through 6, wherein the plurality of deformable elements comprises at least four deformable elements.

Example 8

The surgical instrument of any of the previous Examples, wherein the sealing portion extends proximally from the support portion.

Example 9

The surgical instrument of any of the previous Examples, wherein the sealing portion includes an annular sealing edge configured to sealingly engage the inner surface of the shaft.

Example 10

The surgical instrument of any of Example 9, wherein the annular sealing edge is spaced axially from the support portion by an annular groove formed in an exterior of the nodal support element.

Example 11

The surgical instrument of any of the previous Examples, wherein the support portion has an axial length greater than an axial length of the sealing portion.

Example 12

The surgical instrument of any of the previous Examples, wherein the waveguide includes a nodal flange at the distal-most acoustic node, wherein the ultrasonic blade integrally joins with the waveguide at the nodal flange, wherein an interior of the support portion includes an annular groove configured to receive the nodal flange.

Example 13

The surgical instrument of any of the previous Examples, wherein the shaft comprises an inner tube and an outer tube, wherein the nodal support element engages an inner surface of the inner tube.

Example 14

The surgical instrument of any of the previous Examples, wherein the end effector further comprises an RF electrode, wherein the RF electrode is operable to seal tissue with RF energy.

Example 15

The surgical instrument of any of the previous Examples, wherein the end effector further comprises a clamp arm movable relative to the ultrasonic blade to clamp tissue therebetween, wherein the clamp arm provides a first RF electrode, wherein the ultrasonic blade provides a second RF electrode, wherein the first and second RF electrodes are operable to seal tissue with bipolar RF energy.

Example 16

A surgical instrument comprising: (a) an ultrasonic transducer; (b) a shaft extending distally relative to the ultrasonic transducer along a longitudinal shaft axis; (c) a waveguide acoustically coupled with the ultrasonic transducer and extending distally through the shaft; (d) an end effector arranged at a distal end of the shaft, wherein the end effector includes an ultrasonic blade acoustically coupled with the waveguide, wherein the ultrasonic transducer is operable to drive the waveguide and the ultrasonic blade with ultrasonic energy; and (e) a nodal support element positioned to support a nodal portion of the waveguide within the shaft, wherein the nodal support element includes a plurality of deformable elements configured to deform against an inner surface of the shaft.

Example 17

The surgical instrument of Example 16, wherein the nodal support element encircles a distal-most acoustic node of the waveguide.

Example 18

The surgical instrument of any of Examples 16 through 17, wherein the nodal support element further comprises an annular sealing edge spaced axially from the deformable elements, wherein the annular sealing edge is configured to sealingly engage the inner surface of the shaft to prevent proximal ingress of fluid through the shaft.

Example 19

A surgical instrument comprising: (a) an ultrasonic transducer; (b) a shaft extending distally relative to the ultrasonic transducer along a longitudinal shaft axis; (c) a waveguide acoustically coupled with the ultrasonic transducer and extending distally through the shaft, wherein the waveguide includes a distal nodal flange; (d) an end effector arranged at a distal end of the shaft, wherein the end effector includes an ultrasonic blade acoustically coupled with the waveguide, wherein the ultrasonic transducer is operable to drive the waveguide and the ultrasonic blade with ultrasonic energy; and (e) a nodal support element arranged within a distal portion of the shaft, wherein the nodal support element comprises: (i) a plurality of protrusions configured to engage an inner surface of the shaft and thereby support the waveguide within the shaft, and (ii) a wiper seal spaced axially from the protrusions, wherein the wiper seal is configured to sealingly engage the inner surface of the shaft and thereby prevent proximal ingress of fluid through the shaft.

Example 20

The surgical instrument of Example 19, wherein the nodal support element encircles the waveguide, wherein the protrusions are spaced circumferentially about an outer surface of the nodal support element.

Example 21

A surgical instrument comprising: (a) an ultrasonic transducer; (b) a shaft extending distally relative to the ultrasonic transducer along a longitudinal shaft axis; (c) a waveguide acoustically coupled with the ultrasonic transducer and extending distally through the shaft; (d) an end effector arranged at a distal end of the shaft, wherein the end effector includes an ultrasonic blade acoustically coupled with the waveguide, wherein the ultrasonic transducer is operable to drive the waveguide and the ultrasonic blade with ultrasonic energy; and (e) a nodal support element arranged within a distal portion of the shaft, wherein the nodal support element encircles the waveguide at a distal-most acoustic node thereof, wherein the nodal support element includes an annular rim that defines a maximum outer diameter of the nodal support element, wherein the annular rim is configured to sealingly engage an inner surface of the shaft with an interference fit to thereby support the waveguide in coaxial alignment with the shaft axis and prevent proximal ingress of fluid through the shaft.

Example 22

The surgical instrument of example 21, wherein the nodal support element is formed of a resiliently deformable material Example 23

The surgical instrument of example 21, wherein the nodal element further comprises (i) a proximal tapered portion arranged proximally of the annular rim, and (ii) a distal tapered portion arranged distally of the annular rim.

Example 24

The surgical instrument of example 23, wherein the nodal element further comprises a distal flap that extends distally from the distal tapered portion.

Example 25

The surgical instrument of example 21, wherein the waveguide includes a nodal flange at the distal-most acoustic node, wherein the ultrasonic blade integrally joins with the waveguide at the nodal flange, wherein the nodal support element encircles the nodal flange.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. Pat. patent application Ser. No. 15/967,740, entitled "Combination Ultrasonic and Electrosurgical Instrument Having Electrical Circuits With Shared Return Path," filed on May 1, 2018; published as U.S. Pub. No. 2018/0333177 on Nov. 22, 2018; U.S. Pat. patent application Ser. No. 15/967,746, entitled "Combination Ultrasonic and Electrosurgical Instrument Having Slip Ring Electrical Contact Assembly," filed on May 1, 2018, issued as U.S. Pat. No. 10,945,778 on Mar. 16, 2021; U.S. Pat. patent application Ser. No. 15/967,747, entitled "Combination Ultrasonic and Electrosurgical Instrument Having Electrically Insulating Features," filed May 1,2018; issued as U.S. Pat. No. 10,945,779 on Mar. 16, 2021; U.S. Pat. patent application Ser. No. 15/967,751, entitled "Combination Ultrasonic and Electrosurgical Instrument Having Curved Ultrasonic Blade," filed on May 1, 2018, published as U.S. Pub. No. 2018/0333180 on Nov. 22, 2018; U.S. Pat. patent application Ser. No. 15/967,753, entitled "Combination Ultrasonic and Electrosurgical Instrument Having Clamp Arm Electrode," filed May 1, 2018, published as U.S. Pub. No. 2018/0333181 on Nov. 22, 2018;

U.S. Pat. patent application Ser. No. 15/967,761, entitled "Combination Ultrasonic and Electrosurgical System Having Generator Filter Circuitry," filed on May 1, 2018 published as U.S. Pub. No. 2018/0333184 on Nov. 22, 2018; and/or U.S. Pat. patent application Ser. No. 15/967,764, entitled "Combination Ultrasonic and Electrosurgical System Having EEPROM and ASIC Components," filed on May 1, 2018, published as U.S. Pub. No. 2018/0333186 on Nov. 22, 2018. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. Pat. patent application Ser. No. 15/967,758, entitled "Combination Ultrasonic and Electrosurgical Instrument with Clamp Arm Position Input and Method for Identifying Tissue State," filed May 1, 2018, published as U.S. Pub. No. 2018/0333182 on Nov. 22, 2018; U.S. Pat. patent application Ser. No. 15/967,763, entitled "Combination Ultrasonic and Electrosurgical Instrument with Adjustable Energy Modalities and Method for Sealing Tissue and Inhibiting Tissue Resection," filed on May 1, 2018, published as U.S. Pub. No. 2018/0333185 Nov. 22, 2018; U.S. Pat. patent application Ser. No. 15/967,770, entitled "Combination Ultrasonic and Electrosurgical Instrument with Adjustable Clamp Force and Related Methods," filed on May 1, 2018, published as U.S. Pub. No. 2018/0333187 on Nov. 22, 2018; U.S. Pat. patent application Ser. No. 15/967,775, entitled "Combination Ultrasonic and Electrosurgical Instrument with Adjustable Energy Modalities and Method for Limiting Blade Temperature," filed on May 1, 2018, published as U.S. Pub. No. 2018/0333188 on Nov. 22, 2018; U.S. Pat. patent application Ser. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 on Nov. 22, 2018; and/or U.S. Pat. patent application Ser. No. 15/967,784, entitled "Combination Ultrasonic and Electrosurgical Instrument and Method for Sealing Tissue in Successive Phases," filed on May 1, 2018, published as U.S. Pub. No. 2018/0333190 on Nov. 22, 2018. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use.

Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) an ultrasonic transducer;
   (b) a shaft extending distally relative to the ultrasonic transducer along a longitudinal shaft axis;
   (c) a waveguide acoustically coupled with the ultrasonic transducer and extending distally through the shaft, wherein the waveguide has a distal nodal flange at a distal-most acoustic node;
   (d) an end effector arranged at a distal end of the shaft, wherein the end effector includes an ultrasonic blade acoustically coupled with the waveguide, wherein the ultrasonic transducer is operable to drive the waveguide and the ultrasonic blade with ultrasonic energy; and
   (e) a nodal support element arranged within a distal portion of the shaft, wherein the nodal support element encircles the waveguide at the distal nodal flange and the distal-most acoustic node thereof, wherein the nodal support element comprises:
      (i) a support portion aligned with the distal-most acoustic node and including a plurality of deformable elements, wherein the support portion is configured to engage an inner surface of the shaft and thereby support the waveguide in coaxial alignment with the longitudinal shaft axis such that each of the plurality of deformable elements radially projects perpendicular to the longitudinal shaft axis and is radially aligned with the distal nodal flange, wherein the plurality of deformable elements define at least one space angularly therebetween about the longitudinal shaft axis,
      (ii) a sealing portion extending axially from the support portion, wherein the sealing portion is configured to sealingly engage the inner surface of the shaft and thereby prevent proximal ingress of fluid through the shaft, and
      (iii) an outer annular groove longitudinally between the plurality of deformable elements and the sealing portion.

2. The surgical instrument of claim 1, wherein the nodal support element comprises an overmold member.

3. The surgical instrument of claim 1, wherein the support portion has a maximum outer diameter that is greater than an inner diameter of the shaft, wherein the support portion is configured to engage the inner surface of the shaft with an interference fit.

4. The surgical instrument of claim 1, wherein the plurality of deformable elements are spaced circumferentially about an exterior of the support portion, wherein the deformable elements are configured to deform against the inner surface of the shaft.

5. The surgical instrument of claim 4, wherein the deformable elements are resiliently deformable.

6. The surgical instrument of claim 4, wherein the deformable elements are arranged with uniform circumferential spacing.

7. The surgical instrument of claim 4, wherein the plurality of deformable elements comprises at least four deformable elements.

8. The surgical instrument of claim 1, wherein the sealing portion extends proximally from the support portion.

9. The surgical instrument of claim 1, wherein the sealing portion includes an annular sealing edge configured to sealingly engage the inner surface of the shaft.

10. The surgical instrument of claim 9, wherein the annular sealing edge is spaced axially from the support portion by the outer annular groove formed in an exterior of the nodal support element.

11. The surgical instrument of claim 1, wherein the support portion has an axial length greater than an axial length of the sealing portion.

12. The surgical instrument of claim 1, wherein the ultrasonic blade integrally joins with the waveguide at the distal nodal flange, wherein an interior of the support portion includes an annular groove configured to receive the distal nodal flange.

13. The surgical instrument of claim 1, wherein the shaft comprises an inner tube and an outer tube, wherein the nodal support element engages an inner surface of the inner tube.

14. The surgical instrument of claim 1, wherein the end effector further comprises a radiofrequency (RF) electrode, wherein the RF electrode is operable to seal tissue with RF energy.

15. The surgical instrument of claim 1, wherein the end effector further comprises a clamp arm movable relative to the ultrasonic blade to clamp tissue therebetween, wherein the clamp arm provides a first RF electrode, wherein the ultrasonic blade provides a second RF electrode, wherein the first and second RF electrodes are operable to seal the clamped tissue with bipolar RF energy.

16. A surgical instrument comprising:
(a) an ultrasonic transducer;
(b) a shaft extending distally relative to the ultrasonic transducer along a longitudinal shaft axis;
(c) a waveguide acoustically coupled with the ultrasonic transducer and extending distally through the shaft;
(d) an end effector arranged at a distal end of the shaft, wherein the end effector includes an ultrasonic blade acoustically coupled with the waveguide, wherein the ultrasonic transducer is operable to drive the waveguide and the ultrasonic blade with ultrasonic energy; and
(e) a nodal support element having an exterior and positioned to support a nodal portion of the waveguide within the shaft, wherein the nodal support element includes a plurality of deformable elements spaced circumferentially about the exterior and configured to deform against an inner surface of the shaft.

17. The surgical instrument of claim 16, wherein the nodal support element encircles a distal-most acoustic node of the waveguide.

18. The surgical instrument of claim 16, wherein the nodal support element further comprises an annular sealing edge spaced axially from the deformable elements, wherein the annular sealing edge is configured to sealingly engage the inner surface of the shaft to prevent proximal ingress of fluid through the shaft.

19. A surgical instrument comprising:
(a) an ultrasonic transducer;
(b) a shaft extending distally relative to the ultrasonic transducer along a longitudinal shaft axis;
(c) a waveguide acoustically coupled with the ultrasonic transducer and extending distally through the shaft, wherein the waveguide includes a distal nodal flange;
(d) an end effector arranged at a distal end of the shaft, wherein the end effector includes an ultrasonic blade acoustically coupled with the waveguide, wherein the ultrasonic transducer is operable to drive the waveguide and the ultrasonic blade with ultrasonic energy; and
(e) a nodal support element arranged within a distal portion of the shaft, wherein the nodal support element comprises:
(i) a plurality of protrusions configured to engage an inner surface of the shaft and thereby support the waveguide within the shaft, and
(ii) a wiper seal spaced axially from the plurality of protrusions, wherein the wiper seal is configured to sealingly engage the inner surface of the shaft and thereby prevent proximal ingress of fluid through the shaft
wherein each of the plurality of protrusions is longitudinally spaced from the wiper seal, and
wherein each of the plurality of protrusions radially projects perpendicular to the longitudinal shaft axis and is radially aligned with the distal nodal flange, wherein the plurality of protrusions define at least one space angularly therebetween about the longitudinal shaft axis.

20. The surgical instrument of claim 19, wherein the nodal support element encircles the waveguide, wherein the plurality of protrusions are spaced circumferentially about an outer surface of the nodal support element.

* * * * *